(12) United States Patent
Varenne et al.

(10) Patent No.: US 6,398,757 B1
(45) Date of Patent: Jun. 4, 2002

(54) GENE THERAPEUTIC TREATMENT OF BLOOD VESSEL ASSOCIATED DISORDERS

(75) Inventors: Olivier Henry Varenne, Brussels; Désiré José Collen, Winksele; Stefan Pierre Janssens, Heverlee, all of (BE)

(73) Assignees: Leuven Research & Development VZW, Leuven; Vlaams Interuniversitair Instituut voor Biotechnologie, Zwijnaarde, both of (BE)

( * ) Notice: Subject to any disclaimer, the term of this patent is extended or adjusted under 35 U.S.C. 154(b) by 0 days.

(21) Appl. No.: 09/367,014

(22) PCT Filed: Feb. 9, 1998

(86) PCT No.: PCT/EP98/00723

§ 371 (c)(1),
(2), (4) Date: Oct. 26, 1999

(87) PCT Pub. No.: WO98/34667

PCT Pub. Date: Aug. 13, 1998

(51) Int. Cl.⁷ ............................................. A61M 29/00
(52) U.S. Cl. ................................................ 604/103.02
(58) Field of Search ................................. 606/108, 194, 606/192; 604/103.01, 103.02, 183, 191

(56) References Cited

U.S. PATENT DOCUMENTS 6,197,013 B1 * 3/2001 Reed et al. ............ 604/103.01

FOREIGN PATENT DOCUMENTS

| EP | 0753322 | 1/1997 |
|----|---------|--------|
| EP | 0768098 | 4/1997 |
| WO | 9211895 | 7/1992 |
| WO | 9605321 | 2/1996 |

\* cited by examiner

*Primary Examiner*—Kevin Truong
(74) *Attorney, Agent, or Firm*—Webb Ziesenheim Logsdon Orkin & Hanson, P.C.

(57) ABSTRACT

A catheter containing an inflatable balloon, which is at its periphery provided with hollow extensions that communicate between the outside of the balloon and the lumen of the catheter for use in the gene therapeutic treatment of local disorders by transfer of a desired gene to a target cell or tissue being part of or being located in the vicinity of a blood vessel. The catheter is preferably the Infiltrator® catheter.

6 Claims, 4 Drawing Sheets

GENE THERAPEUTIC TREATMENT OF BLOOD VESSEL ASSOCIATED DISORDERS

BACKGROUND OF THE INVENTION

The present invention relates to a catheter for use in gene therapeutic treatment of local disorders by transfer of a desired gene to a target cell or tissue being part of or being located in the vicinity of a blood vessel. The present invention in a first preferred embodiment relates more in particular to the local transfer of the nitric oxide synthase (Ms) gene into the wall of arteries injured by interventional procedures such as angioplasty or stenting. In another preferred embodiment the invention relates to the gene therapeutical treatment of vasculated tumors by transfer of genes encoding a product that may kill or inhibit growth of tumor cells and/or vascular cells.

Gene therapy as intended by the present invention involves the genetic engineering of cells of a subject in need or therapy. Through genetically engineering cells they will acquire one or more desirable properties they did not or did no longer possess, for example the ability to express a particular protein. As an alternative a cell may be genetically engineered to loose an unwanted property.

Conditions that can be treated by means of gene therapy through local delivery of a gene of interest to a target cell or tissue are for example restenosis and cancer.

Restenosis is a complex biological process, initiated by platelet adhesion and aggregation at the site of arterial injury Platelet activation results in the release of a variety of vasoactive, growth, and mitogenic factors that stimulate vascular smooth muscle cell (VSMC) proliferation and migration, matrix formation, and the late fibroproliferative response. In addition, injury to the endothelial protective barrier results in the loss of constitutively expressed endothelium-derived vasoactive factors including nitric oxide (NO), prostacyclin and bradykinin, which under normal circumstances play an important role in vascular homeostasis.

Over the past 15 years, percutaneous transluminal coronary angioplasty (PTCA) has significantly altered the management of symptomatic coronary artery disease. Despite its overall value in achieving immediate symptomatic relief, restenosis occurs in 30 to 50% of patients within 3 to 6 months. Restenosis following PTCA is caused by progressive elastic recoil, extracellular matrix formation, and fibrointimal hyperplasia at the site of angioplasty. However, in randomized clinical trials most currently used pharmacological agents have failed to demonstrate any beneficial effect on restenosis. The need therefore exists for a new form of treatment of this condition. Gene therapy is a very promising prospect. Local transfer of genes encoding antiproliferative and angiogenic proteins has been effective in animal models of neointima formation following angioplasty in peripheral arteries.

All established tumors, both primary and metastasized, that are larger than a few millimeter in diameter are vascularized. In addition, distant metastases usually emerge after migration of tumor cells from the primary tumor through the blood or lymphatic circulation. Thus, all solid tumors are in close contact with the circulation and, in principle, could be reached via the circulation. Gene therapeutically influencing tumor cells via the circulation is therefore very well possible. Moreover, killing of a solid tumor does not necessarily depend on gene transfer into the tumor cells themselves. Gene therapy strategies have been proposed where genetic material (e.g., the HSV-tk gene) is introduced into endothelial cells of the tumor vasculature (e.g., WO96/21416). This should result in destruction of the tumor vasculature, ultimately leading to tumor necrosis.

Gene therapeutic treatment of conditions like restenosis and cancer that are associated with blood or lymphatic vessels can thus be accomplished via the circulation.

However, the first important step in genetically engineering cells in gene therapy is being capable of efficiently transferring a vector harboring the gene of interest to the cell.

Local adenoviral-mediated vascular gene transfer is currently accomplished by different delivery devices, including double balloon, coated balloon and microporous balloon catheters, which by virtue of their design have only resulted in limited vascular gene transfer in animal models. The double balloon catheter creates an isolated space within the artery for instillation of vectors, but delivery/transduction efficacy is hampered by side branches within the central space of the lumen. A balloon catheter coated with a hydrophilic polymer containing plasmid DNA is currently used in a human gene therapy protocol for angiogenesis in peripheral arteries, but is less suited for coronary gene transfer because of washout after exposure to the blood stream. Microporous balloon catheters allow local high pressure delivery with jet-lesion formation including intimal disruption, medial dissection, or subintimal haemorrhage but result in limited transgene expression in the coronary vessel wall of large animals.

In view of the above problems encountered in local delivery of vectors for gene therapy to vessel walls or the vicinity of vessels with the help of catheters, it is the object of the present invention to provide the possibility of a more efficient local vector transfer system than is currently available, in particular for use in the treatment of conditions and disorders associated with or occurring in the vicinity of blood vessels, such as restenosis and solid tumors.

BRIEF SUMMARY OF THE INVENTION

This object is achieved by means of using a catheter containing an inflatable balloon, which is at its perifery provided with hollow extensions that communicate between the outside of the balloon and the lumen of the catheter for use in the gene therapeutic treatment of local disorders by transfer of a desired gene to a target cell or tissue being part of or being located in the vicinity of a blood vessel. A particularly suitable catheter is the Infiltrators® catheter.

DETAILED DESCRIPTION OF THE INVENTION

In a preferred embodiment the catheter can be used for treatment comprises therapy or prophylaxis of restenosis by the local transfer of the nitric oxide synthase (NOS) gene into the wall of arteries injured by interventional procedures such as angioplasty or stenting. In an alternative embodiment the treatment comprises treatment of vasculated tumors by transfer of genes encoding a product that may kill or inhibit growth of tumor cells and/or vascular cells.

Figure 1:
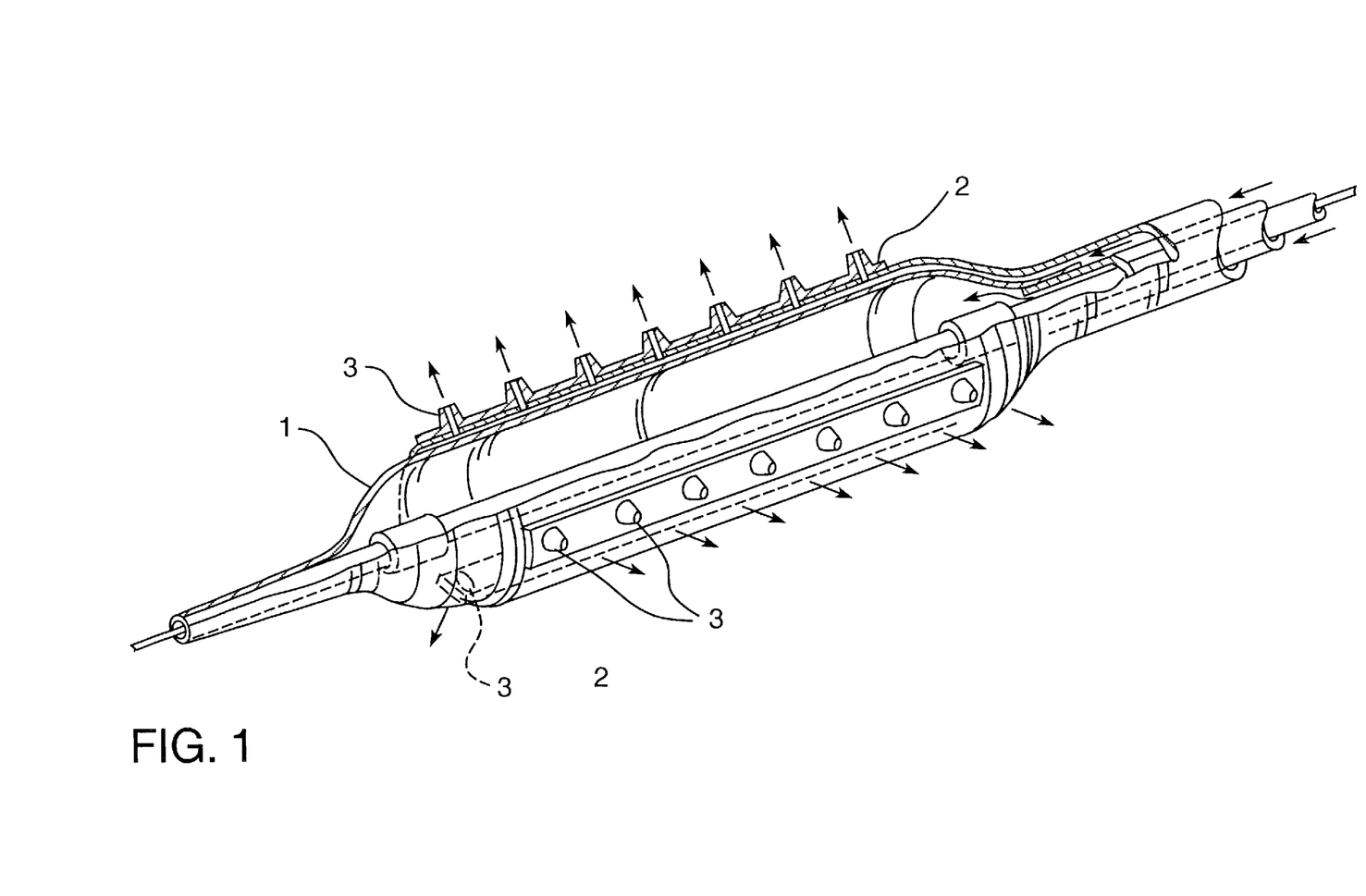
FIG. 1 is a cutaway view of a balloon and lumen catheter suitable for use in the present invention.

In a preferred embodiment of the invention the delivery of the vector to the target cell or tissue is accomplished by means of a catheter as disclosed in European patent applications no. 753 322 and no. 768 098. In a particularly preferred embodiment the catheter is the so-called Infiltrators® (InterVentional Technologies Inc., San Diego, Calif. USA), a multi-lumen balloon catheter allowing PTCA and simultaneous local intramural delivery of vectors. The Infiltrator® is a non-compliant angioplasty balloon (2.0–4.0 mm), covered by three injector plates, each containing seven injector microports (height 0.254 mm, exit width 0.102 mm) which are recessed in the balloon during introduction in the artery (FIG. 1). Once the balloon is inflated to 1 to 2 atmospheres, the microports radially protrude through the internal plastic lamina (IEL) of the arterial wall. A separate lumen allows intramural vector delivery through all three channels over a short period of time (<15 seconds) via hand injection. The fluid infiltration (400 $\mu$l) via this catheter causes mild, localized, medial edema without intimal damage or separation of the vessel layers.

The recombinant vectors for use in the present invention are selected from the following: retroviral vectors, adenoviral vectors, adeno-associated vectors, herpes vectors, plasmids. Of these retroviral vectors and adeno-associated vectors are preferred. The vectors may be incorporated in liposomes.

The treatment can be performed on any blood vessel, in particular arteries or veins that have been injured by interventional procedures, like angioplasty or stenting, As an alternative, the treatment may be performed on vascularized (solid) tumors through delivery of the vectors to the cells or tissues of the vascularized part of the tumor.

The gene of interest that is to be transferred to the target cell or tissue depends on the effect to be achieved.

In the case of injured arteries the gene is for example the nitric oxide synthase (NOS) gene.

Genes affecting local cellular proliferation, migration and neointimal formation in the vessel wall can favorably affect the outcome of the stenotic process. In principal, gene products affecting vascular tone may also influence the sequelae of injury to the vessel wall.

A variety of different genes encoding antiproliferative proteins delivered to cells within the vessel wall reduce neointima formation. They include proteins that act directly on smooth muscle cell proliferation such as cell cycle proteins, toxic gene products, or products of normal endothelium Alternatively, indirectly-acting gene products like vascular endothelial growth factor have been used. The cellular targets of gene transfer have been both endothelium and smooth muscle cells within the media and The retinoblastoma (Rb) gene product functions as a cell cycle inhibitor to inhibit the proliferation of smooth muscle cells that characterize the proliferative response. Adenovirus-mediated gene transfer of a constitutively active, non-phosphorylatable form of Rb reduces smooth muscle cell proliferation and restenosis following balloon angioplasty.

The p21 protein is an important negative regulator of cell cycle progression in mammalian cells that functions by inhibiting cell cycle dependent protein kinases and by binding to proliferating cell nuclear antigen, a DNA polymerase delta cofactor. Adenovirus encoding the p21 protein reduces vascular smooth muscle cell proliferation and neointima formation.

Similarly, gax is a homeobox gene normally expressed by vascular smooth muscle cells that is downregulated following vascular injury to promote the wound-healing response in the vessel wall. In balloon-injured rabbit iliac arteries, adenovirus-mediated gax overexpression in smooth muscle cells prevents neointimal hyperplasia and luminal stenosis, but does not affect re-endothelialization and endothelium-dependent vasomotion.

The herpes simplex virus Thymidine kinase (tk) gene functions as a selectively toxic gene product when combined with ganciclovir treatment and kills transduced cells, hereby depicting the population of proliferating cells within the target tissue. Local adenovirus-mediated gene transfer of tk has been demonstrated to reduce neointima formation by 50% in injured porcine arteries, and the BrdU labeling index by 65% and neointima formation by 50% in a rabbit hyperlipidemic injury model.

Vascular endothelial growth factor (vegf) is an endothelial mitogen which acts to promote re-endothelialization of the vessel wall, limit the exposure of underlying smooth muscle cells to mitogenic stimuli, and thereby reduce the neointimal proliferation of smooth muscle cells following balloon injury of normal vessels. In a rabbit model of atherosclerosis, local adenovirus-mediated vegf gene transfer has been shown to increase the minimal luminal diameter and thus reduce the degree of post-angioplasty stenosis. In another study, an adenovirus vector expressing the specific clotting inhibitor hirudin was used to locally transduce smooth muscle cells and inhibit active thrombin in an injured rat carotid model systemic effects on clotting were not observed as evidenced by unchanged partial thromboplastin times, but neointima formation in the vessel was inhibited by 35%. The rationale underlying this study is that the inhibition of thrombin reduces the exposure of the injured vessel segment to cytokines anchor growth factors released locally at the site of injury by activated monocytes, andothelial tells, or platelets within a blood clot.

The constitutive endothelial nitric oxide synthase (ceNOS) enzyme is responsible for the local production of nitric oxide (NO). ceNOS gene transfer smooth muscle cells in rat carotid arteries denuded of endothelium by balloon injury can also have profound local effects. By increasing cGMP levels and inhibiting smooth muscle cell proliferation at the site of injury, ceNOS gene transfer is an effective therapy to reduce neointima formation within the injured segment.

furthermore, antimigratory proteins can also be used to inhibit the process of smooth muscle cell migration that characterizes cellular remodeling of the vessel wall, The serpin plasminogen activator inhibitor 1 (PAI-1), a specific inhibitor of both urinary plasminogen activator (uPA) and tPA, is another attractive candidate protein to treat vascular stenosis based on the results of gene targeting experiments in mice. The results obtained with vascular injury models in mice lacking genes encoding various components of the fibrinolytic system demonstrate that plasminogen activation is involved in the process of smooth muscle cell migration and vascular stenosis. Further, mice lacking urinary plasminogen activator (uPA) responsible for cellular plasminogen activation and degradation of extracelular matrix show significant reductions in the vascular wound healing response that leads to stenosis, while conversely, plasminogen activator inhibitory (PAI-1) deficient mice are hyperstenotic and show accelerated smooth muscle cell migration and proliferation responses. PAI-1 gene transfer into PAI-1 knockout mice has been performed using adenovirus-mediated gene transfer Into the liver to augment systemic expression of PAI-1. The results demonstrate that restoration of circulating PAI-1 into such mice can suppress the vascular wound healing response and dramatically reduce the degree of vascular stenosis which develops following injury. Interestingly, no deleterious side effects on homeostasis by PAI-1 overexpression have been observed in these mice.

In related studies on degradation of the extracellular matrix by vascular smooth muscle cell expression of metalloproteinases, adenovirus-mediated overexpression of the tissue inhibitor of metalloproteinase-2 (TIMP-2) was found to inhibit smooth muscle cell migration through Matrigel in vitro, which can also be a useful strategy in vivo. Since plasminogen activation has been shown to activate matrix metalloproteinases, this observation supports the hypothesis that uPA is a primary mediator of smooth muscle cell migration and neointimal thickening. Conversely, gene transfer in normal rabbits has been shown to increase neointimai thickening and augment contractile responses in vein grafts transduced by a recombirant adenovirus vector expressing TGFB1-transduced vessels which increases smooth muscle cell migration and proliferation in the vessel wall.

Genes whose expression will alter vascular tone can also have significant effects on blood vessel remodeling and other processes. For example, NO or endothelium-derived relaxing factor, has potent relaxation properties on blood vessels. Instillation of adenovirus into the lumen in normal rabbit vessels and endothelial cell gene transfer using virus encoding ceNOS results in augmented ceNOS synthesis, increases in basal CGMP levels, and both diminish contractile responses to phenylephrine and enhanced relaxations to acetylcholine. Similarly, gene transfer of β2-adrenergic receptors was shown to augment expression six-fold and thus enhance the vasorelaxation induced by isoproterenol in de-endothelialized rat carotid arteries. Conversely, adenoviral gene transfer of the endothelin cDNA to the livers of rats led to pathophysiologic levels of endothelin expression and systemic hypertension mediated by the ETA receptor.

The effects described hereinabove are in part previously published observations. However, they are indications that a broader scope of protection than gene therapeutic treatment with NOS as described in the Examples alone is indeed justified. NOS has been used as a model system to show that the method of the invention is indeed very effective. This is not an effect that is limited to the NOS gene but applies to other genes suitable for gene therapeutically treating restenosis as well.

The same applies to the treatment of cancer. The genes that can be brought into a tumor cell or its vicinity may encode molecules that can be used to kill tumor cells. Such molecules include but are not restricted to suicide enzymes that convert a non-toxic prodrug into a toxic compound (e.g. the HSV-tk/ganciclovir system), cytokines, antisense nucleic acid molecules, ribozymes, and tumor suppressor proteins (such as, e.g. the Retinoblastoma or p53 gene products). In addition, treatment of cancer by gene therapy methods also includes the delivery of replicating adenovectors that are toxic to the tumor cells by themselves.

Gene therapy by introduction of nucleic acid molecules encoding suicide enzymes has been widely tested on a variety of tumor models. Especially the transfer of the Herpes simplex virus thymidine kinase (HSV-tk) gene into tumor cells in conjunction with systemic administration of the non-toxic substrate ganciclovir has proven to be an effective way of killing tumor cells in vivo. An important advantage of the HSV-tk/ganciclovir system is that upon ganciclovir treatment HSV-tk transduced tumor cells mediate a significant killing effect on neighboring untransduced tumor cells, the so-called bystander effect. Thus, using this approach there is no absolute need for gene transfer into every individual cell in a solid tumor to achieve successful gene therapy.

In an alternative embodiment the gene to be transferred can encode a cytokine. Gene therapy for cancer by the introduction of nucleic acid molecules encoding cytokines is based on the concept of enhancing the immune response against the tumor cells. The ultimate goal of this approach is to obtain regression of the treated tumor and simultaneously induce such a high degree of immunity that coexisting metastases are also destroyed. Compared to direct administration of a cytokine protein the gene transfer approach as suggested by the present invention has the important advantage of high-level production of the cytokine at the site of the tumor, while systemic concentrations of the cytokine remain low. This avoids any pleiotropic and toxic side effects associated with said cytokine, Signs of (partially) successful cancer treatment have been described for tumor cells expressing IL- 1, IL-2, IL-3, IL-4, interferon-gamma, interferon-alpha, TNF-alpha, IL-7, G-CSF, GM-CSF, and IL- 12, The present invention further enhances the efficacy of these treatments.

Killing of tumor cells can also be accomplished by introducing into said tumor cells genetic information that comprises or encodes nucleic acid molecules with a sequence complementary to that of a nucleic acid molecule that needs to be expressed in said tumor cell. The introduced nucleic acid molecule or copies made thereof in situ prevent the translation of said nucleic acid molecule that needs to be expressed in said tumor cell into its encoded protein by specific base pairing. The tumor cells will then die as a consequence of a shortage in said encoded protein.

A similar effect can be achieved by introducing into said tumor cells a nucleic acid molecule that encodes or is itself a so-called ribozyme or deoxyribozyme. In this case said nucleic acid molecule or copies made thereof in situ are capable of specifically cleaving a nucleic acid molecule that needs to be expressed in said tumor cells, Also in this case, the tumor cells will die as a consequence of a shortage in said encoded protein.

Another similar effect can be achieved by introducing into said tumor cells a nucleic acid molecule that encodes or is itself a so-called decoy molecule, in this case said nucleic acid molecule or copies made thereof in situ (nucleic acid molecules or proteins) are capable of specifically binding to a protein molecule that needs to be functionally expressed in said tumor cells. Functional expression here means that said protein molecule is capable of exerting its natural biological activity, at least in kind but preferably also in amount. The specific binding results in functional inactivation of said protein molecule that needs to be functionally expressed in said tumor cells. The tumor cells will then die as a consequence of a shortage in functional expression of said protein.

The present invention will be illustrated in the following examples that are, however, not intended to be limiting the scope of the invention.

The present invention is illustrated in these Examples on the basis of reduction of neointima formation and arterial restenosis following injury by gene transfer in the porcine coronary artery which is injured by percutaneous transluminal angioplasty (PTA). The local delivery is carried out with the Infiltrator® catheter which ensures efficient viral transduction of medial smooth muscle cells (SMC) and of adventitial cells, resulting in increased local nitric oxide (NO) production and reduced smooth muscle cell proliferation and migration.

In addition, control studies were performed on the efficacy of the Infiltrator® for gene transfer into the vessel wall. These studies demonstrated that the Infiltrator® catheter enabled highly efficient local gene transfer in the media and adventitia of coronary arteries.

Furthermore, experiments were performed on the therapeutic effect of adenovirus-mediated delivery of the cDNA encoding NOS, the enzyme responsible for the formation of nitric oxide (NO) from L-arginine in intact blood vessels. NOS is either constitutively expressed in endothelium (ceNOS or type III), induced by cytokines in a variety of cell types (iNOS or type II) or constitutively expressed in the brain (nNOS or type I). NO inhibits platelet aggregation, leukocyte adhesion, and VSMC proliferation and migration in vitro, and may be an important endogenous inhibitor of vascular lesion formation in vivo. Oral administration of L-arginine, the precursor of NO, is known to inhibit neointimal thickening 4 weeks after balloon denudation of normocholesterolemic rabbit iliac arteries. Recently, ceNOS gene transfer in the vessel wall, using the Sendai virus/liposome mediated gene transfer technique, showed a 70% reduction of neointima formation in the rat carotid artery, but rats are notoriously sensitive to pharmological and molecular modulation of neointima formation. In the present invention, a high efficacy of intracoronary ceNOS gene transfer was demonstrated and a significant reduction in arterial restenosis at 28 days after balloon angioplasty in pigs, which respond to injury with a morphologic and pharmacosensitive pattern much more similar to that of arterial restenosis in man.

The results of the Examples can be summarized as follows: (1) the Infiltrator® catheter allows a highly efficient local adenoviral-mediated transfer of genes, including NOS, into the medial and adventitial cell layers of non injured and balloon-injured coronary arteries, (2) no transduction is observed in distal or unrelated coronary arteries, and (3) adenoviral-mediated transfer of cDNA encoding ceNOS restores vascular CGMP levels following balloon injury and significantly reduces coronary restenosis 28 days after angioplasty, primarily via an effect on neointima formation.

In the Examples reference is made to the following figures:

FIG. 1. The Infiltrator® catheter incorporates a low pressure positioning balloon 1 with three longitudinal strips 2 of seven micro-miniaturized injector ports 3 mounted on its surface. When the positioning balloon is inflated, the injector microports radially extend and intrude a 15 mm vessel wall fragment at 120 ° angles.

Figure 2:
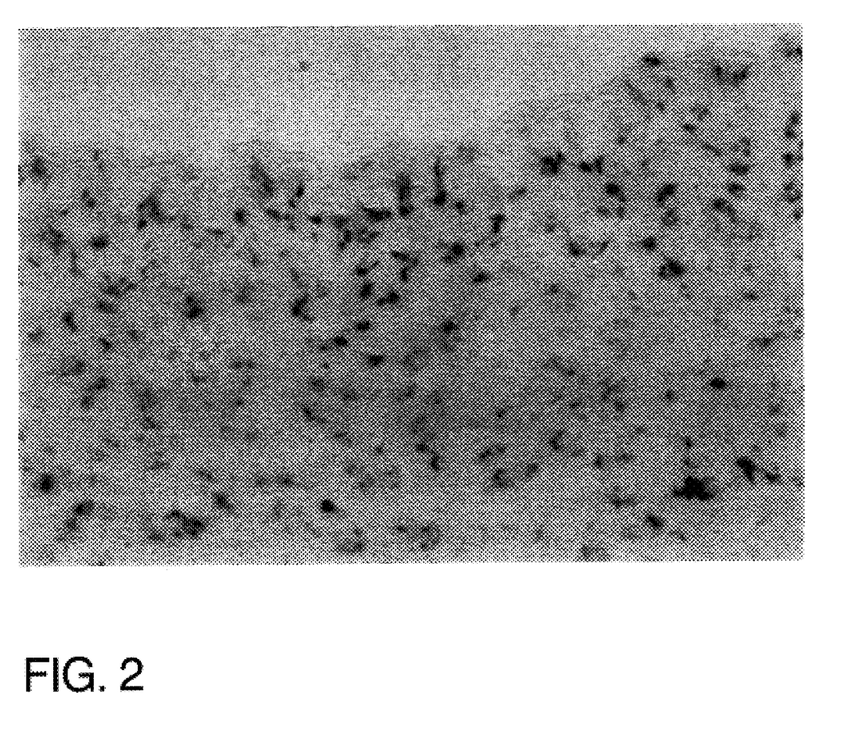
FIG. 2 is a photomicrograph illustrating vascular cells post-therapy.

FIG. 2. Photomicrograph illustrating the distribution of β-galactosidase expressing vascular cells following local AdCMV gal gene transfer in the LAD coronary artery. Recombinant, replication-deficient adenovirus carrying a nuclear-localizing variant of the E. coli β-galactosidase cDNA (AdCMV gal, 300 µl, 5×10$^9$ pfu/ml) was injected in porcine coronary arteries using the Infiltrator® catheter. Marked transgene expression is observed in medial SMCs and throughout the adventitia. The dark spots represent the β-galactosidase.

Figure 3:
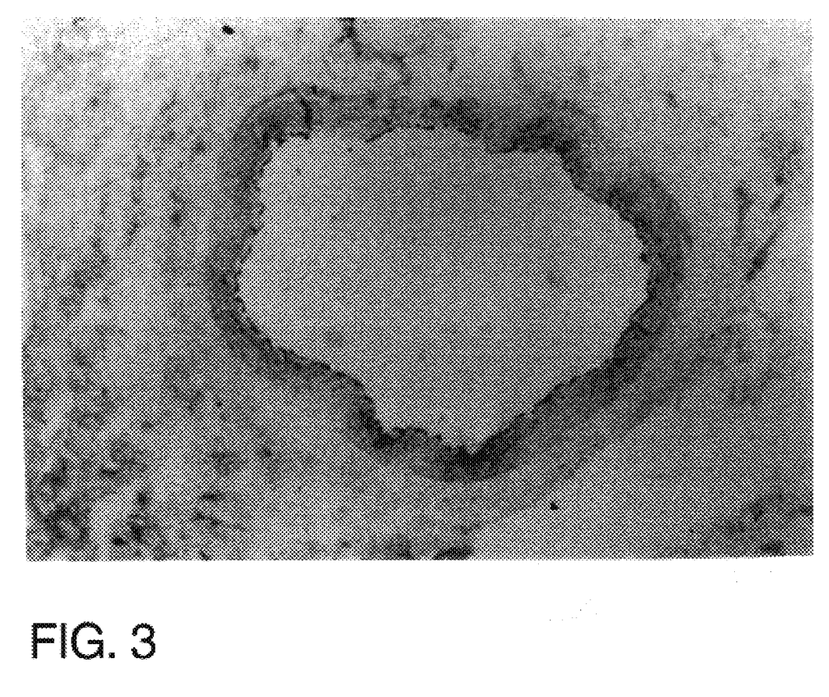
FIG. 3 is a photomicrograph illustrating the distribution of transgenic vascular cells post-therapy.

FIG. 3. Photomicrograph illustrating the distribution of ceNOS expressing vascular cells following AdCMvceNOS gene transfer in the LAD coronary artery as revealed by immunostaining for ceNOS. Marked transgene expression is observed in the medial and adventitial cell. layers.

Figure 4:
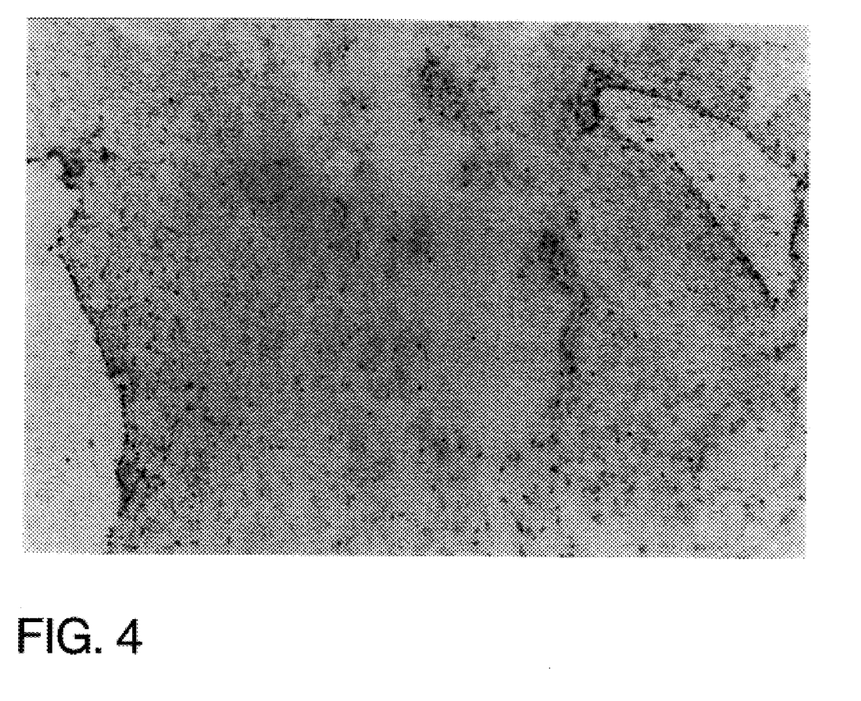
FIG. 4 is a photomicrograph of a cross section of a control LAD artery.

FIG. 4. Cross section of a control LAD artery from an uninfected animal, showing diffuse endogenous ceNOS immunoreactivity in luminal endothelial cells and in endothelial cells of vasa vasorum and a coronary side branch.

Examples 1

Construction and Purification of Recombinant Adenovirus

Recombinant adenovirus containing the human constitutive endothelial nitric oxide synthase (ceNOS) cDNA was constructed, and amplified as previously described (Jaxisens et al., J. Clin. Invest. (1996) 98(2).317–324). Briefly, a 3.7-kilobaae fragment of cDNA encoding human ceNOS (Janssen et al., J. Biol. Chem. (1992) 267(3)) was cloned between the enhancer/promoter of the cytomegalovirus (CMV) immediate early genes and the SV40 polyadenylation signal of the bacterial plasmid pACCMVpLpA (Gomez-Foix et al., J. Biol. Chem. 267:25129–25134 (1992)). The plasmid also contains ElA-deleted sequences of type 5 adenovirus including the origin of replication, the packaging signal and the pUC19 polylinker.

Recombinant adenovirus was generated through homologous recombination with PJM17, a bacterial plasmid derived from the E3-deletion mutant dl309 (Bett et al., Virus Res. 39:75–82 (1995)), following cotransfection in ElA-transformed human embryonic kidney (293) cells (Graham et al., J. Gen. Virol. 36:59–72 (1977)). The recombinant virus is both E1- and E3-deleted. ceNOS-containing viral isolates (AdCMVceNOS) were amplified on confluent 293 cells and, after appearance of cytopathic effects, were isolated, precipitated, and concentrated by discontinuous CsCl gradient ultracentrifugation. For all in vivo studies, viral titers were adjusted to $5 \times 10^9$ plaque forming units (pfu)/ml.

Recombinant adenovirus containing the inducible NOS (iNOS) cDNA was constructed using similar procedures. In addition recombinant adenovirus containing the LacZ gene encoding a nuclear-localizing variant of the E. coli β-galactosidase cDNA (AdCMVβgal (Herz & Gerard, PNAS 90:2812–2816 (1993))), and similar constructs carrying the hirudin cDNA (AdCMvHir, construct made in the CTG by Dr P. Zoldhelyi), or no cDNA (AdRR5 (Kopler et al., Clin. Res. 41:211A (1993))) were used to evaluate gene transfer efficiency, recombinant protein production or to serve as control virus.

Example 2

Adenovirus-mediated NOS Gene Transduction and Validation of Recombinant Protein Activity In Vitro Porcine vascular smooth muscle cells (VSMCs) were cultured in DMEM supplemented with l0o fetal bovine serum (Gibco BRL, N.V. Life Technologies, Merelbeke, Belgium), 50 units/ml penicillin and 50 g/ml streptomycin. The cells were grown in chamber slides (Nunc Inc., Naperville, Ill. USA) to approximately 60% confluence and infected with AdCMVceNOS or AdRR5 diluted in DMEM supplemented with 2% fetal bovine serum at 2, 20, and 200 pfu per cell. After 24 hours, the viral suspension was removed, and the cells were maintained in culture for 3 days.

The third day following infection, the cells were washed with phosphate-buffered saline (PBS), fixed for 20 minutes in 4% paraformaldehyde and washed twice in 1 mmol/L Tris, 0.9% NaCl, 0.1% Triton X 100 (Merck, Darmstadt, Germany), buffer pH 7.6 (Tris-buffered saline, TBS): Cells were preincubated with rabbit pre-immune serum (dilution 1.5) in TBS for 45 minutes and incubated overnight with a monoclonal mouse anti-human ceNOS antibody 2 µg/ml (1:125 dilution) (Transduction Laboratories, Exeter, UK), followed by incubation for 1 hour with a rabbit anti-mouse IgG antibody complexed to horseradish peroxidase (dilution 1:200) (Vector Laboratories Inc., Burlingame, USA). Antibody binding was visualized with diaminobenzidine tetrahydrochloride (DAB) in 0.1 mol/L Tris buffer containing 0.03% $H_2O_2$, pH=7.2. PBS was used to wash the slides between incubation steps. Slides were counterstained with Harris' hematoxylin, dehydrated, and mounted with D.P.X. compound (Prosan, Gent. Belgium).

Cytoplasmic ceNOS immunoreactivity was observed in AdCMVceNOS-infected VSMCs but not in AdRR5-infected VSMCs. The number of positive SMCs for ceNOS-immunostaining was proportional to the multiplicity of infection (MOI) applied (45%±2% at MOI 2, 88%±4% at MOI 20, and 100%±1% at MOI 200). Recombinant ceNOS expression after AdCMvceNOS infection Won also Confirmed by immunoblot analysis. Similar results were obtained with AdCMViNOS in cultured rat aortic SMCs.

ceNOS is an nicotinamide adenine dinucleotide phosphate (NADPH)- and tetrahydrobiopterin-dependent enzyme which catalyzes the oxidation of the terminal guanidino nitrogen of L-arginine to L-citrulline, with generation of NO. Electron transfer from reduced NADPH to nitroblue tetrazolium is accompanied by a colour change, which can be detected by histochemical staining. Porcine VSMCs were infected for 24 hours with AdCMVceNOS or with a AdRR5 (2, 20 or 200 pfu/cell) as described above. The medium was changed 24 hours after infection, and cells were harvested at 72 hours and incubated in 0.2 mmol/L nitroblue tetrazolium with 1 mmol/L NADPH in 0.1 mol/L Tris-HCl, pH7.2, and 0.2% Triton X-100 for 30 minutes at 37° C. A dark blue cytoplasmic staining pattern indicated NOS-dependent diaphorase activity and confirmed the presence of functional enzyme. The number of cells expressing NADPH-diaphorase activity was similar to the number of ceNOS positive VSMCs. AdRR5-infected cells did not show NADPH-diaphorase activity at the MOI's applied.

Example 3

Gene Transfer Following PTCA in the Coronary Arteries in Pigs

All animal care and handling were performed in accordance with the guidelines specified in the National Institutes of Health "Guide for Care and Use of Laboratory Animals" and were approved by the Animal Care and Use Committee of the University of Leuven. Juvenile domestic pigs weighing 20–25 kg were treated with aspirin 300 mg orally, 5 days per week, starting the day of surgery. They were anesthetized with an intravenous bolus of azaperone 0.1 ml/kg, pentobarbital 10 mg/kg and keta-mine 5 mg/kg, followed by an intravenous infusion of ketamine 10 mg/kg/h. The pigs were intubated and ventilated with $O_2$ enriched-room air. ECG and arterial pressure were monitored continuously throughout the experiment. After exposure of the right carotid artery, a 8F left Judkins guiding catheter was introduced through a 8F sheath and advanced to the base of the aorta. The left main coronary ostium was then engaged and a commercial, non compliant 3.0 mm balloon dilatation catheter was advanced over a standard 0.014 inch flexible wire into the left anterior descending (LAD) coronary artery, and positioned distal to the first diagonal branch, Arterial injury was achieved by three 30 seconds inflations at 10 atmospheres with a 1 minute reflow between each inflation. The balloon was deflated and removed and the Infiltrator® catheter was advanced to the site of injury. The inflation of the Infiltrator® balloon at 2 atmospheres was followed by hand injection over 10 seconds of 0.3 ml of recombinant virus (titer-5×10$^9$ pfu/ml). The Infiltrator® catheter was deflated, withdrawn and the right carotid artery ligated. Heparin was given during the experiment as a bolus of 15,000 IU intra-arterially. After surgical repair of the neck cutdown the animals were allowed to recover. Intramuscular enrofloxacine, 0.5 ml/10 kg, was administered for the first 3 days following the intervention. The animals were given normal chow and were reanesthetized 4 weeks later for control coronary angiography. They were then sacrificed by saturated KCl injection and the coronary arteries were harvested for morphometric analysis of the injured arterial segment as described below.

Example 4

Adenovirus-Mediated Gene Transfer Efficiency In Vivo

To assess gene transfer efficiency of the Infiltrator® catheter in the coronary vessel wall, 4 pigs were instrumented as described above, and were infected with 300 µl AdCMVβal (titer 5×10$^9$ pfu/ml) after balloon angioplasty. Intracoronary gene transfer was also performed in 2 uninjured pigs. At day 4, the pigs were sacrificed, the heart quickly removed, and the LAD was cannulated, perfused with 4% formaldehyde under 100 $cm_2O$ . pressure for 4 hours, and washed with PBS for 24 hours. To identify the cells expressing the transgene, the artery was cut into 2-mm rings, and cells expressing the LacZ gene were detected using β-galactosidase staining (3.3 mmol/L $K_3Fe(CN)_6$, 3.3 mmol/L $K_4Fe(CN)$, 1 mmol/L $MgCl_2$ and 1 mg/ml 5-bromo-4-chloro-3-indolyl-β-D-galactopyranoside, in Na phosphate buffer, pH=7) for 8 hours at 37° C. The arterial rings were then washed in PBS and 5 µm paraffin sections at 0.2-mm intervals were prepared and counterstained with nuclear fast red (Sigma, Bornem, Belgium) (FIG. 2). The number of medial and adventitial cells with blue coloration of their nuclei was counted in the area of maximal transduction, and expressed as a ratio over the total number of cells.

In uninjured coronary arteries infected with AdCMVgal, marked β-galactosidase activity was detected in medial and in adventitial cells, with occasional blue staining in the surrounding myocytes. The percent of β-galactosidase positive cells at the site of maximal transduction was 41±10% in the media, and 23±3% in the adventitia (FIG. 2). The β-galactosidase positive cells were mostly present in the outer layers of the media and in the internal layers of the adventitia. No nuclear blue staining was observed in the coronary arterial segments infected with ADRR5 or AdCMVceNOS. The IEL was ruptured at the site of penetration of the injector microports without medial tear or rupture of the external elastic lamina (EEL). The number of β-galactosidase positive cells was markedly increased around the site of the injector microports. In the arteries subjected to PTCA prior to viral infection, the injury was more pronounced with tear of the medial layers and intramural hematoma.

To quantitate recombinant protein production in vivo following intracoronary gene transfer, porcine coronary arteries were transduced with AdaMVHir (5×10$^9$ pfu/ml). Secretion of recombinant hirudin in conditioned medium from explanted porcine coronary arterial segments was measured by ELISA. Conditioned medium was changed daily from 3 to 7 and occasionally up to 10 days after gene transfer. Briefly, the wells of a high-binding microtiter plate were incubated 48 hours at 4° C. with 1.0 g/ml of a monoclonal anti-r-hirudin antibody obtained from Ciba-Geigy. Then, the coated plates were washed four times and blocked with 2t bovine serum albumin (BSA) in phosphate-buffered saline (PBS) containing 0.05% Tween 20 for 2 hours at room temperature. The plates were washed and conditioned medium and purified hirudin standards were applied to the wells for 2 hours at room temperature. A horseradish peroxidase-conjugated sheep antibody recognizing r-hirudin (1:8000 dilution in PBS) was added to the wells and incubated for 2 hours at room temperature.

Antibody binding was visualized by a 15-minutes incubation at room temperature with orthophenylene diamine (OPD) in citrate buffer, pH 5.0. The reaction was stopped with 4 mol/L sulfuric acid and the absorbance read at 492 nm. The detection limit of the ELISA (defined as lowest concentration giving a signal above the mean+2SD of the background) was 15 pg/ml. Recombinant hirudin production in conditioned medium from Ad-CMVhirudin-infected coronary arteries increased from 49 pg/ml at day 3 to 200 pg/ml at day 7. After 7 days, the secretion decreased and was no longer detectable at day 10. No hirudin secretion was detected in untransduced right coronary arteries.

Example 5

Recombinant ceNOS Expression in the Vessel Wall Following Intramural Gene Delivery Recombinant ceNOS expression in coronary arteries after AdCMVceNOS infection was evaluated immunohistochemically on frozen arterial sections. Four pigs were infected with 300 μl AdCMVceNOS (titer $5 \times 10^9$ pu/tml) and sacrificed at day 4. Coronary arteries were harvested as described.

5.1 ceNOS Immunostaining

Arterial rings were embedded in O.C.T. compound (Miles Inc., Diagnostics Division Elkhart, USA) and immediately frozen in liquid nitrogen. Coronary artery sections (5 m) were fixed for 20 minutes in ice-cold methanol, washed, and incubated overnight with a monoclonal mouse anti-human ceNOS antibody 2 μg/ml (dilution 1:125) (Transduction Laboratories, UK) followed by incubation for 30 minutes in methanol containing 3% $H_2O_2$. The detailed experimental conditions are described in example 2. Biotinylated rabbit anti-mouse antibody (dilution 1:200) was used as secondary antibody (Vector Laboratories Inc., Burlingame, USA) and antibody binding visualized by streptavidin-conjugated horseradish peroxidase (ABC kit, Dako). Diffuse ceNOS immunostaining was observed throughout the adventitia and in the outer cell layers of the media (FIG. 3). In control arteries, only little ceNOS immunoreactivity was detected in endot-helial cells of vasa vasorum, but no ceNOS immunoreactivity was observed in medial SMCs (FIG. 4), 5.2 NADPH-diaphorase Staining Four days after AdCMVceNOS infection 5 μm coronary artery cryosections were incubated with 0.2 mmol/L nitroblue tetrazolium and 1 mmol/L NADPH in 0.1 mol/L Tris-HCl, pH 7.2, and 0.2% Triton X-100 for 45 minutes at 37° C. Uninjured, untranaduced coronary artery was used as control. Intense dark blue cytoplasmic staining, indicative of NADPH-diaphorase activity, was observed in the medial cells after infection. While this was seen in untransduced endothelium, NOS-dependent diaphorase activity Was not detected in the media of uninjured arteries or in injured porcine arteries infected with AdRR5.

5.3 cGMP Measurements

No increases cGMP levels via stimulation of soluble guanylate cyclase. To test the ability of recombinant ceNOS protein to generate NO, cGMP production in the vessel wall was measured using a commercial enzyme immunoassay (Amersham Life Science, Belgium). Frozen coronary arterial segments from AdCMvceNOS-transduced, control injured and normal arteries (n=4, each) were homogenized in 1 ml ice-cold 6% trichloroacetic acid (TCA), pH 4.0, and centrifuged at 10,000 g for 15 minutes at 4° C. The supernatant was transferred into a 30-ml glass centrifuge tube and TCA was extracted four times with $H_2O$-saturated ether. A 500 μl aliquot of the sample was then lyophilized, resuspended in 500 μl of 0.05 M sodium acetate buffer, pH 5.8, and assayed for cGMP. Vascular cGMP levels were expressed as pmoles cGMP per mg of TCA-precipitable protein. Vascular cGMP levels in untransduced injured arteries were significantly lower than in uninjured coronary arteries (0.33±0.20 vs 1.3±0.42 pmol/mg protein, P=0.002). Adenoviral-mediated overexpression of ceNOS increased vascular cGMP levels after injury to levels found in untransduced, uninjured arteries (1.8±0.98 pmol/mg protein).

Example 6

Effect of Local ceNOS Gene Delivery on Arterial Stenosis in Pigs

In this study, 25 animals underwent local gene transfer with the Infiltrator® catheter following balloon angioplasty of the LAD coronary artery. Intramural gene delivery was carried out with AdCMVceNOS (n=12) or AdRR5 (n=13). There were no significant differences in body weight, age, or gender between the two groups. (Table 1) The balloon to artery diameter ratio was similar in both groups, excluding difference in balloon injury as a confounding variable.

TABLE 1.

Group characteristics.

| Characteristics | AdRR5 (n = 13) | AdCMVceNOS (n = 12) | P value |
|---|---|---|---|
| Body weight (kg) | 26 3 | 25 2 | ns |
| sex | 7/6 (F/M) | 5/6 (F/M) | ns |
| death | 1 | 1 | ns |
| Balloon to artery diameter ratio | 1.60 0.08 | 1.65 0.09 | ns |
| occlusive thrombus | 2 | 0 | ns |
| Pericarditis | 2/13 | 1/12 | ns |
| Myocardial infarction | 2/13 | 0/12 | ns |
| Final analysis | 10/13 | 10/12 | ns |

Twenty eight days after gene transfer, the pigs were sacrificed under general anaesthesia by a lethal dose of saturated potassium chloride solution. The coronary arteries were harvested, fixed with 4% formalin at 100 cm $H_2O$ for three hours. The injured coronary segment was then carrefully dissected from the epicardial surface and sectioned transversely into 2 mm rings, washed, and embedded in paraffin. Five μm thick sections were cut every 100 μm and stained with Haemaluin and Eosin (H&E) for subsequent analysis. Cross-sectional areas of the intima and media were measured by an experienced observer blinded to the origin of the samples, using a computarized morphometric analysis system (TCI Image, C. N. Rood N. V., Brufsel, Belgium; Media Cybernetics, Silver Spring, Maryland USA). The borders of the external elastic lamina (MeL), internal elastic lamina (IEL), and vessel lumen were traced on a digitizing board and the areas bounded by each were calculated. The percentage area stenosis (100×(1-lumen area/IEL, area), and the intima (I) to media (M) ratio (I/M ratio) were determined. The maximal (neo)intimal thickness (in mm) of each analyzed section was measured, and the extent of the injury was further assessed by the ratio of IEL fracture length to IEL circumference. Animals were excluded if an occlusive thrombus was detected (in 2 pigs given AdRR5 and in none given AdCMvceNOS). Random sections were reviewed by a second observer blinded to the treatment assignment.

Results are presented as mean ±SD. The paired Student's t-test was used to compare percentage area stenosis, maximal intimal thickening, residual lumen area, and neointima area divided by IEL fracture length between the two groups. Differences were considered Significant at $p<0.05$.

H&E and Verhoeffs-Van-Gieson-stained sections from all arterial segments were examined. A small number of sections in AdRR5-infected arteries showed the presence of a hematoma in the media-adventitia dissection plains as a result of the angioplasty, or occlusive thrombus. No intramyocardial hemorrhage was observed.

Arteries transduced with AdRR5 showed a marked neointima at 28 days, consisting mostly of stellate and spindle-shaped cells in a loose extracellular matrix. In the majority of the samples, there was complete coverage of the luminal surface by a monolayer of endothelium-like cells. In AdCMVceNOS-treated animals, the neointimal area normalized to the IEL fracture length and the maximal neointimal thickness were significantly smaller than in AdRR5-infected arteries (0.80±0.19 vs 0.59±0.14 mm (p=0.011), and 1.04±0.25 vs 0.75±0.21 mm (p=0.012) respectively).

TABLE 2.

Results of morphometric analysis of coronary artery segments at 28 days after injury.

| | AdRR5 (n = 10) | | AdCMVceNOS (n = 10) | | P value |
|---|---|---|---|---|---|
| EEL area (mm$^2$) | 2.27 | 0.52 | 2.55 | 0.79 | ns |
| IEL fracture length/IEL (%) | 0.40 | 0.10 | 0.43 | 0.13 | ns |
| Maximal Neointimal Thickness (mm) | 1.04 | 0.25 | 0.75 | 0.21 | 0.012 |
| Lumen area (mm$^2$) | 0.32 | 0.18 | 0.70 | 0.35 | 0.007 |
| Neointimal area/IEL | 0.80 | 0.19 | 0.59 | 0.14 | 0.011 |
| fracture length (mm) Stenosis (%) | 75 | 11 | 53 | 15 | 0.001 |

What is claimed is:

1. A medical device comprising a catheter containing an inflatable balloon, which catheter is provided at its periphery with hollow extensions that communicate between the outside of the balloon and a lumen of the catheter for use in the gene therapeutic treatment of local disorders by transfer of a desired gene to a target cell or tissue being part of or being located in the vicinity of a blood vessel.

2. The catheter as claimed in claim 1, wherein the treatment comprises therapy or prophylaxis of restenosis by the local transfer of the nitric oxide synthase (NOS) gene into the wall of arteries injured by interventional procedures such as angioplasty or stenting.

3. The catheter as claimed in claim 1, wherein the treatment comprises treatment of vasculated tumors by transfer of genes encoding a product that may kill or inhibit growth of tumor cells and/or vascular cells.

4. A method for administering gene therapy comprising:

1) locating within a blood vessel in an area of an animal or patient to be treated a distal end of a catheter containing an inflatable balloon, said catheter being provided at its periphery with hollow extensions that communicate between the outside of the balloon and a lumen of the catheter; and 2) passing through said lumen and said hollow extensions at least one gene therapy active agent to deliver said agent to said area.

5. The method according to claim 4, wherein said gene therapy active agent is nitric oxide synthase (NOS) in an amount effective to treat injuries in vessel walls due to interventional procedures such as angioplasty or stenting.

6. The method according to claim 4, wherein said gene therapy active agent is selected from the group consisting of a gene therapy anticancer agent and a gene therapy antivascular agent.

* * * * *

UNITED STATES PATENT AND TRADEMARK OFFICE
CERTIFICATE OF CORRECTION

PATENT NO. : 6,398,757 B1
DATED : June 4, 2002
INVENTOR(S) : Olivier Henry Varenne et al.

It is certified that error appears in the above-identified patent and that said Letters Patent is hereby corrected as shown below:

<u>Title page,</u>
Insert :
-- [30] Foreign Application Priority Data
Feb. 7, 1997    (EP)................................ 97200330-5 --.

<u>Column 1,</u>
Line 11, "(Ms) gene" should read -- (NOS) gene --.
Line 19, "or therapy." should read -- of therapy. --.
Line 29, after "arterial injury" insert period.

<u>Column 3,</u>
Line 31, between "stenting" and "As" delete comma and insert period.
Lines 49-50, between "endothelium" and "Alternatively" insert period.
Line 53, after "media and" insert -- adventitia. --.

<u>Column 4,</u>
Line 37, "andothelial tells" should read -- endothelial cells --.
Line 47, "furthermore" should read -- Furthermore --.
Line 49, between "wall" and "The" delete comma and insert period.
Line 67, "transfer Into" should read -- transfer into --.

<u>Column 5,</u>
Line 20, "TGFBI" should read -- TGF$\beta$1 --.

<u>Column 6,</u>
Line 20, between "cytokine" and "Signs" delete comma and insert period.
Line 41, between "cells" and "Also" delete comma and insert period.
Line 47, "decoy molecule, in" should read -- decoy molecule. In --.

<u>Column 7,</u>
Line 67, between "cell" and "layers" delete period.

UNITED STATES PATENT AND TRADEMARK OFFICE
CERTIFICATE OF CORRECTION

PATENT NO. : 6,398,757 B1
DATED : June 4, 2002
INVENTOR(S) : Olivier Henry Varenne et al.

It is certified that error appears in the above-identified patent and that said Letters Patent is hereby corrected as shown below:

Column 8,
Line 14, "3.7-kilobaae" should read -- 3.7-kilobase --.
Line 52, "with l0o" should read -- with 10% --.

Column 9,
Line 19, "Won also" should read -- was also --.
Lines 19-20, "also Confirmed" should read -- also confirmed --.
Line 65, between "branch" and "Arterial" delete comma and insert period.

Column 10,
Line 5, "titer-" should read -- titer= --.
Line 25, "AdCMV$\beta$al" should read -- AdCMV$\beta$al --.
Line 29, "100 cm$_2$O" should read -- 100 cm H$_2$O --.
Line 34, "K$_4$Fe(CN)" should read -- K$_4$Fe(CN)$_6$ --.

Column 10,
Line 52, "ADRR5" should read -- AdRR5 --.
Line 63, "AdaMVHir" should read -- AdCMVHir --.

Column 11,
Line 33, "AdCMvceNOS" should read -- ,AdCMVceNOS, --.
Line 33, "pu/tml)" should read -- pfu/ml --.
Line 56, after "(FIG. 4)" delete comma and insert period.
Line 63, "untranaduced" should read -- untransduced --.
Line 67, "activity Was" should read -- activity was --.

Column 12,
Line 5, "No increases" should read -- NO increases --.
Line 10, "AdCMvceNOS" should read -- AdCMVceNOS --.
Line 67, "computarized" should read -- computerized --.

UNITED STATES PATENT AND TRADEMARK OFFICE
CERTIFICATE OF CORRECTION

PATENT NO.   : 6,398,757 B1
DATED        : June 4, 2002
INVENTOR(S)  : Olivier Henry Varenne et al.

It is certified that error appears in the above-identified patent and that said Letters Patent is hereby corrected as shown below:

<u>Column 13,</u>
Line 1, "Brufsel, Belgium" should read -- Brussel, Belgium --.
Line 3, "(MeL)" should read -- (EEL) --.
Line 6, between "IEL" and "area)" delete comma.
Line 13, "AdCMvceNOS" should read -- AdCMVceNOS --.
Line 19, "considered Significant" should read -- considered significant --.

Signed and Sealed this

Eleventh Day of March, 2003

JAMES E. ROGAN
*Director of the United States Patent and Trademark Office*